United States Patent
O' Lenick, Jr.

[11] Patent Number: 6,087,522
[45] Date of Patent: Jul. 11, 2000

[54] SILICONE LANOLIN ESTERS

[75] Inventor: Anthony J. O'Lenick, Jr., Dacula, Ga.

[73] Assignee: Fan Tech Corporation, Chicago, Ill.

[21] Appl. No.: 09/415,253

[22] Filed: Oct. 12, 1999

[51] Int. Cl.[7] .................................................. C07F 7/08

[52] U.S. Cl. ......................... 556/437; 556/440; 552/544

[58] Field of Search ..................................... 556/437, 440; 552/544

[56] References Cited

U.S. PATENT DOCUMENTS

| | | |
|---|---|---|
| 4,069,347 | 1/1978 | McCarthy . |
| 4,428,885 | 1/1984 | Higaki et al. ............................ 552/544 |
| 4,537,722 | 8/1985 | Stamvik et al. ........................ 552/544 |
| 4,549,990 | 10/1985 | Seguin et al. ........................... 552/544 |

*Primary Examiner*—Paul F. Shaver

[57] ABSTRACT

Lanolin eaters of silicones are prepared by reacting a carboxy silicone and lanolin alcohol to form an ester. The resultant products are useful as highly water resistant lubricating coatings for skin.

12 Claims, No Drawings

SILICONE LANOLIN ESTERS

The invention discloses novel lanolin esters of silicone compounds which an ester linkage, and a silicone polymer. Compounds of the invention are made by reacting (a) a carboxy silicone, and (b) lanolin alcohol to form an ester. Compounds of the invention by virtue of (i) the silicone group, (ii) the ester group and (iii) the lanolin alcohol containing group all contribute to a unique highly effective spreadable lubricating coating that have an outstanding feel on skin.

The reaction used to prepare the compounds of the present invention is an esterification of a carboxy silicone and lanolin alcohol. The resulting ester provides effective water resistant coatings that have an outstanding feel on skin, as such they are recommended for barrier creams and hand lotions. The incorporation of the lanolin alcohol into a silicone backbone results not only in the improved water resistance properties of the compound, but also in minimizing the penetration of the skin by the lanolin alcohol. This in due in part to the increased molecular weight of the lanolin alcohol/silicone polymer.

ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

Lanolin has been used for many years in personal care applications. Lanolin (CAS number 8006-54-0) is a pale yellow paste, obtained from the wool of sheep. It is a waxy ester. Lanolin is used as a topical treatment on skin. Since lanolin is very water insoluble and difficult to formulate into many products, it has been derivitized. Lanolin has been ethoxylated to make water soluble ethoxylates. Generally 75 moles of ethylene oxide is added to obtain the desired solubility. While the ethoxylation provides the desired solubility, the substantivity to the skin and the water resistant properties are sacrificed.

Lanolin, being an ester, is fractionated into the component lanolin alcohol and lanolin fatty acids. The alcohol contains the components that are most interesting for skin care. The acids are not unique in structure, but the alcohols on the other hand are quite unique. The alcohol component is describd below. since lanolin alcohol is a natural product, it is a complex mixture. Historically, lanolin fatty acids have been derivitized to make quaternary compounds. U.S. Pat. No. 4,069,347 to McCarthy issued in 1978 is illustrative of the chemistry.

U.S. Pat. No. 2,752,334 to Conrad issued in 1955 discloses the acetylation of lanolin alcohol. It was not until the compounds of the present invention was the benefit of incorporating silicone onto the lanolin alcohol was discovered. The benefits include (a) the ability to make a water soluble silicone lanolin esters that is truly substantive to skin, (b) the reduction in skin penetration due to elevated molecular weight of the ester, (c) the cosmetically elegant skin feel of the compounds that can be delivered from aqueous systems,and (d) the biodegradation rendered to the molecule by the presence of the ester linkage. All these unexpected properties were heretofore unavailable from compounds of the prior art.

THE INVENTION

OBJECT OF THE INVENTION

It is the object of the present invention to provide an effective highly water resistant coatings that have an outstanding feel on skin. The compounds of the present invention provide (a) the ability to make a water soluble silicone lanolin esters that is truly substantive to skin, (b) for the reduction in skin penetration due to elevated molecular weight of the ester, (c) for cosmetically elegant skin feel of the compounds that can be delivered from aqueous systems, and (d) compounds that biodegrade due to the presence of the ester linkage.

The presence of silicone in the molecule gives superior substantivity to these substrates, the presence of the lanolin alcohol group gives superior water resistivity on the skin. The presence of the ester linkage between the silicone and aromatic group results in a linkage which will biodegrade rapidly in waste water, making the compound less persistent in the waste water stream.

The formation of the ester linkage and the incorporation of the lanolin alcohol group into the silicone of the present invention is accomplished by an esterification reaction of a carboxy silicone and a lanolin alcohol.

SUMMARY OF THE INVENTION

The compounds of this invention are made by the esterification of a carboxy silicone compound and lanolin alcohol. In order to obtain a molecule with the desired attributes, the amount of fluorine is controlled by selection of the particular lanolin alcohol used in the reaction. Only if the compounds are specifically selected will compounds useful in the preparation of the compounds of the present invention be obtained.

Specifically, the compounds of the present invention are esters compounds which is prepared by the esterification reaction of;

(a) a silicone carboxylate conforming to the following structure:

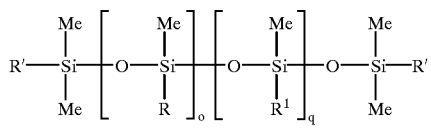

wherein;

Me is methyl;

R and R' are $CH_3$ or $-(CH_2)_3-O-(EO)_a-(PO)_b-(EO)_c-C(O)-R''-C(O)-OH$;

with the proviso that both R and R' are not $CH_3$;

R'' is selected from $-CH_2-CH_2-$; $-CH=CH-$; $-CH_2-C(R^7)-H$;

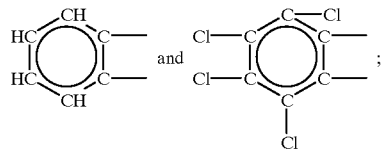

$R^7$ is alkyl having from 1 to 20 carbon atoms;
$R^1$ is selected from lower alkyl $CH_3(CH)_n-$ or phenyl;
n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500.
and (b) lanolin alcohol.

Lanolin alcohol as previously stated is a natural product that is derived by the hydrolysis of lanolin. Lanolin, being an ester, is fractionated into the component lanolin alcohol and lanolin fatty acids. The alcohol contains the components that are most interesting for skin care. The acids are not unique in structure, but the alcohols on the other hand are quite unique.

Lanolin alcohol is composed of;

| Component | % by weight | Range (%) |
|---|---|---|
| Cholesterol | 34.5 | 29.5–39.5 |
| Aliphatic alcohols | 25.0 | 12.5–37.5 |
| Having 18 to 30 carbon atoms) | | |
| Diols | 12.5 | 10.0–15.0 |
| Lanosterol | 10.0 | 3.0–17.0 |
| 3-beta-hydroxy-7-keto-lanst-8-ene | 10.0 | 5.0–15.0 |
| Dihydrolanesterol | 8.0 | 4.0–12.0 |

Compounds of the present invention conform to the following structure:

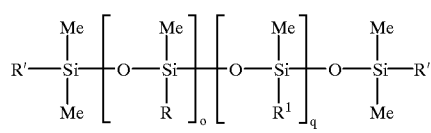

wherein;

Me is methyl;

R and R' are $CH_3$ or $-(CH_2)_3-O-(EO)_a-(PO)_b-(EO)_c-C(O)-R''-C(O)-OR^2$;

with the proviso that both R and R' are not $CH_3$;

R'' is selected from $-CH_2-CH_2-$; $-CH=CH-$; $-CH_2-C(R^7)-H$;

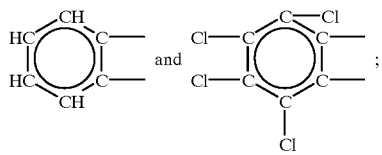

$R^7$ is alkyl having from 1 to 20 carbon atoms;
$R^1$ is selected from lower alkyl $CH_3(CH)_n-$ or phenyl;
n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100:
q is an integer ranging from 0 to 500;
$R^2$ is derived from lanolin alcohol.

PREFERRED EMBODIMENTS

In another preferred embodiment x+y+z is greater than zero.

In another preferred embodiment R'' is $-CH_2-CH_2-$.

In another preferred embodiment R'' is $-CH_2-C(R^7)-H$.

In another preferred embodiment R'' is

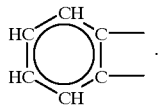

In another preferred embodiment R'' is

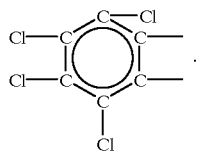

In another preferred embodiment a is 3.
In another preferred embodiment a is 5.
In another preferred embodiment a is 7.
In another preferred embodiment a is 9.
In another preferred embodiment a is 11.
In another preferred embodiment a is 13.
In another preferred embodiment a is 15.
In another preferred embodiment a is 17.

EXAMPLES

The compounds of the present invention are prepared by the reaction of a carboxy silicone compound and lanolin alcohol. Examples of suitable reactants are as follows;

All percentages given are based upon percent by weight, based upon the total weight of the entire batch. All temperatures are degrees C.

Reactants

Lanolin Alcohol

Lanolin alcohol is commercially available from a variety of suppliers, most importantly The Fanning Corporation, Chicago Ill.

Lanolin alcohol is a well known material as well as an item of commerce. It is made up of cholesterol, aliphatic alcohols, having 18 to 30 carbon atoms, diols having 16 to 24 carbon atoms, lanosterol, 3-beta-hydroxy-7-keto-lanst-8-ene, and dihydrolanesterol.

Dimethicone Carboxylate Compounds

Dimethicone Carboxylate compounds are disclosed in U.S. Pat. No. 5,296,625 incorporated herein by reference. They marketed by Siltech Corporation, Toronto Canada under the Silube trade name. The compounds conform to the following structure;

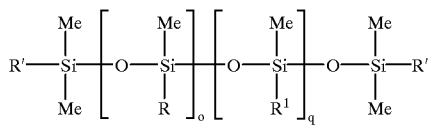

wherein;

Me is methyl;

R and R' are $CH_3$ or —$(CH_2)_3$—O—$(EO)_a$—$(PO)_b$—$(EO)_c$—C(O)—R"—C(O)—OH;

with the proviso that both R and R' are not $CH_3$;

R" is selected from —$CH_2$—$CH_2$—; —CH═CH—; —$CH_2$—$C(R^7)$—H;

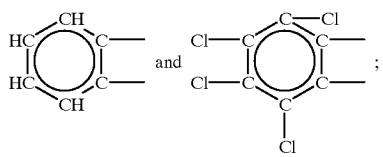

$R^7$ is alkyl having from 1 to 20 carbon atoms;

$R^1$ is selected from lower alkyl $CH_3(CH)_n$— or phenyl;

n is an integer from 0 to 8;

a, b and c are integers independently ranging from 0 to 20;

EO is an ethylene oxide residue —$(CH_2CH_2$—O)—;

PO is a propylene oxide residue —$(CH_2CH(CH_3)$—O)—;

o is an integer ranging from 1 to 100;

q is an integer ranging from 0 to 500.

The carboxy reactants are defined in O'Lenick U.S. Pat. No. 5,296,625 incorporated herein by reference, examples 15–32.

R" Definition

I) O'Lenick Reactant Example I (Succinic Anhydride)

R" is —$H_2C$—$CH_2$—

II) O'Lenick Reactant Example II (Alkyl Succinic Anhydride)

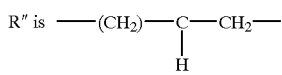

III) O'Lenick Reactant Example III (Alkyl Succinic Anhydride)

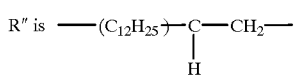

IV) O'Lenick Reactant Example IV (Alkyl Succinic Anhydride)

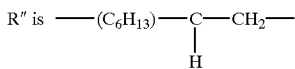

V) O'Lenick Reactant Example V (Alkyl Succinic Anhydride)

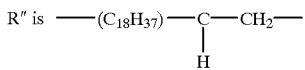

VI) O'Lenick Reactant Example VI (Alkyl Succinic Anhydride)

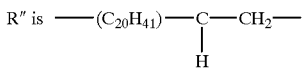

VII) O'Lenick Reactant Example VII (Maleic Anhydride)

R" is —HC═CH—

VIII) O'Lenick Reactant Example VIII (Phthalic Anhydride)

R" is

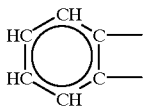

IX) O'Lenick Reactant Example IX (Tetrachlorophthalic anhydride)

R" is

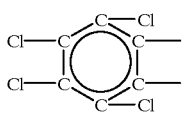

Compounds of the Present Invention

General Reaction Conditions:

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

EXAMPLES

General Procedure

Into a suitable round bottom, three neck flask equipped with a Dean Stark trap, a thermometer and a nitrogen sparge is added the specified number of grams of the carboxy silicone and the specified number of grams of lanolin alcohol and 0.25% of total weight of the batch of catalyst.

The reaction mass is blanketed with nitrogen, and heated to 180 and 200 C. under an inert nitrogen blanket.

Once the reaction temperature reaches 120 C. water begins to boil off and is collected in the Dean Stark Trap. Within four to five hours the theoretical water is collected off and the acid value is very low. The product is used without additional purification.

Example 1

Into a suitable round bottom, three neck flask equipped with a Dean Stark trap, a thermometer and a nitrogen sparge is added 2,450 grams of the carboxy silicone (O'Lenick example 15), 264.0 grams of lanolin alcohol Example 1. and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 2–19

Example 1 is repeated only this time substituting the specified number of grams of the specified carboxy silicone for the carboxy silicone specified and the substituting the specified number of grams of lanolin alcohol.

| | Carboxy Silicone Compound | | | |
|---|---|---|---|---|
| Example | R" Definition | O'Lenick Example | Grams | Lanolin Alcohol Grams |
| 2 | I | 15 | 2,429.0 | 350.0 |
| 3 | II | 16 | 2,147.0 | 350.0 |
| 4 | III | 17 | 5,398.0 | 350.0 |
| 5 | IV | 18 | 533.0 | 350.0 |
| 6 | V | 19 | 4,723.0 | 350.0 |
| 7 | VI | 20 | 3,083.0 | 350.0 |
| 8 | VII | 21 | 3,648.8 | 350.0 |
| 9 | VIII | 22 | 1,722.4 | 350.0 |
| 10 | IX | 23 | 1,288.0 | 350.0 |
| 11 | I | 15 | 2,249.0 | 350.0 |
| 12 | II | 16 | 2,147.0 | 350.0 |

| | Carboxy Silicone Compound | | | |
|---|---|---|---|---|
| Example | R" Definition | O'Lenick Example | Grams | Lanolin Alcohol Grams |
| 13 | III | 17 | 5,398.0 | 350.0 |
| 14 | IV | 18 | 533.0 | 350.0 |
| 15 | V | 19 | 4,723.0 | 350.0 |
| 16 | VI | 20 | 3,083.0 | 350.0 |
| 17 | VII | 21 | 3,648.8 | 350.0 |
| 18 | VIII | 22 | 1,722.4 | 350.0 |
| 19 | IX | 23 | 1,288.0 | 350.0 |

Properties

The compounds of the invention provide water resistant films when applied to skin. The added benefits include (a) the ability to make a water soluble silicone lanolin esters that is truly substantive to skin, (b) the reduction in skin penetration due to elevated molecular weight of the ester, (c) the cosmetically elegant skin feel of the compounds that can be delivered from aqueous systems,and (d) the biodegtadation rendered to the molecule by the presence of the ester linkage. All these unexpected properties were heretofore unavailable from compounds of the prior art.

What is claimed:

1. A compound conforming to the following structure:

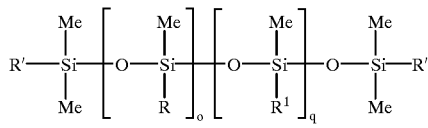

wherein;

Me is methyl;

R and R' are $CH_3$ or $-(CH_2)_3-O-(EO)_a-(PO)_b-(EO)_c-C(O)-R"-C(O)-OR^2$;

with the proviso that both R and R' are not $CH_3$;

R" is selected from $-CH_2-CH_2-$; $-CH=CH-$; $-CH_2-C(R^7)-H$;

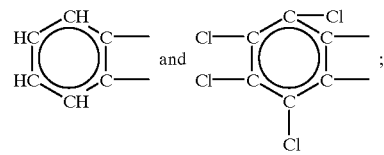

$R^7$ is alkyl having from 1 to 20 carbon atoms;

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500;

$R^2$ is derived from lanolin alcohol.

2. A compound of claim 1 wherein R" is $-CH_2-CH_2-$.

3. A compound of claim 1 wherein R" is $-CH_2-C(R^7)-H$.

4. A compound of claim 1 wherein R" is

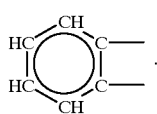

5. A Compound of claim 1 wherein R" is

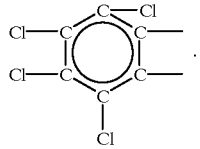

6. A compound of claim 3 wherein $R^7$ is alkyl having from 6 to 20 carbon atoms.

7. A compound of claim 3 wherein $R^7$ is alkyl having from 12 to 20 carbon atoms.

8. A compound of claim 1 wherein a is 9.

9. A compound of claim 1 wherein a is 11.

10. A compound of claim 1 wherein a is 13.

11. A compound of claim 1 wherein a is 15.

12. A compound of claim 1 wherein a is 17.

* * * * *